United States Patent [19]
DiPinto et al.

[11] Patent Number: 5,121,762
[45] Date of Patent: Jun. 16, 1992

[54] WATER SOLUBLE END WRAP AND METHOD OF USE

[75] Inventors: Anthony J. DiPinto; Larry Goldstein, both of Wilmington, Del.; Donald H. Russell, Cherry Hill, N.J.

[73] Assignee: Inno/genics, Inc., Wilmington, Del.

[21] Appl. No.: 553,225

[22] Filed: Jul. 16, 1990

[51] Int. Cl.$^5$ .............................................. A45D 7/04
[52] U.S. Cl. .................... 132/204; 132/221; 132/222
[58] Field of Search ............ 132/222, 221, 204, 203, 132/202

[56] References Cited

U.S. PATENT DOCUMENTS

| | | | |
|---|---|---|---|
| 1,981,362 | 11/1934 | Joyce | 132/222 |
| 2,085,516 | 6/1937 | Thompson | 132/222 |
| 2,140,243 | 12/1938 | Moody et al. | 132/222 |
| 2,688,972 | 9/1954 | Brown | 132/203 |
| 2,832,357 | 4/1958 | Powers | 132/221 |
| 3,141,463 | 7/1964 | Hatton | 132/221 |
| 3,157,578 | 11/1964 | Zviak | 132/204 X |
| 3,345,993 | 10/1967 | Haefele | 132/207 |
| 3,465,759 | 9/1969 | Haefele | 132/207 |
| 3,837,349 | 9/1974 | Jedzinak et al. | 132/207 |
| 3,910,290 | 10/1975 | Litman | 132/221 |
| 3,954,104 | 5/1976 | Kraskin et al. | 604/15 |
| 4,044,782 | 8/1977 | Adrion et al. | 132/207 |
| 4,099,976 | 7/1978 | Kraskin et al. | 604/16 X |
| 4,273,143 | 6/1981 | Klemm et al. | 132/204 |
| 4,371,084 | 2/1983 | Weinrauch | 211/126 |
| 4,600,028 | 7/1986 | Edman et al. | 132/221 |
| 4,615,346 | 10/1986 | Messina et al. | 132/200 |
| 4,632,132 | 12/1986 | Bustance et al. | 132/222 |
| 4,709,712 | 12/1987 | Brodovsky et al. | 132/200 |
| 4,732,169 | 3/1988 | Van Sickle | 132/248 |
| 4,841,997 | 6/1989 | Petrow | 132/204 |
| 4,844,103 | 7/1989 | Vick et al. | 132/245 |

FOREIGN PATENT DOCUMENTS 0098854 8/1979 Japan .................................... 132/221

OTHER PUBLICATIONS

Edman et al. "Permanent wave-patent review", *Cosmetics & Toiletries,* Apr. 1979, pp. 35-38.
Lee et al., "Permanent Waves: An Overview", *Cosmetics & Toiletries,* May 1988, pp. 38-56.
Charles Fox "Hair Products Patent Review and Update", *Cosmetics & Toiletries,* Apr. 1985, pp. 57-76.
ZOTOS Ingredient Dictionary and Technical Terms, pp 183-193.
Hair Structure and Permanent Waves, pp. 10-19, 98 & 99.

*Primary Examiner*—John J. Wilson
*Assistant Examiner*—Jeffrey A. Smith
*Attorney, Agent, or Firm*—Ratner & Prestia

[57] ABSTRACT

An end wrap comprising a substrate containing hair-waving chemicals. Also disclosed is a method for waving hair comprising applying end wraps having hair-waving chemicals to hair sections, activating the end wraps and dissolving the end wraps. A kit for use in the method is included.

23 Claims, No Drawings

WATER SOLUBLE END WRAP AND METHOD OF USE

FIELD OF THE INVENTION

The present invention generally relates to the permanent waving of hair, specifically to cold waving. Permanent waving by the cold waving method involves chemical reactions to achieve the desired result. The invention is directed to end papers, a method of waving hair, and a kit to facilitate the method.

BACKGROUND

Hair is comprised primarily of keratin, a polyamide cross-linked by disulfide bonds. The disulfide bonds are responsible for the hair being maintained in a particular configuration.

Permanent waving is a common technique of styling hair by permanently forming or setting the hair into a desired configuration. Cold permanent waving of hair has been a popular means for waving hair since the 1930's. This popularity is due to the greater convenience of this method over other methods in which externally applied heat is needed to achieve the desired result. This additional convenience has permitted non-professionals to wave their hair in their own homes.

In cold waving, a reducing agent is applied to the hair, causing the hair to be "softened," i.e., the disulfide linkages present in the keratin are broken. This reducing step may be done after sectioning hair into individual tresses, but before rolling it onto curlers, after the rolling has been accomplished, or at both times. After sufficient time has elapsed, the hair is rinsed and neutralized by chemical or air oxidation, reforming the disulfide linkages broken in the reducing step.

Cold permanent waving is not without is problems, however. The materials are often difficult to use and the desired result is not always achieved. The ends of the hair present handling problems and hair damage is common. In the process, the free ends of the hair must be wound about a cylindrical body, a curler, and this presents some difficulty. To overcome this problem, most commercial waving kits contain small square or rectangular pieces of paper or other material known as end wraps which are folded and placed around a hair tress so as to embrace the free end of the tress.

Among materials used for end wraps are permeable polyester and polyether polyurethanes as disclosed by Haefele in U.S. Pat. No. 3,345,993; impermeable polyester and polyether polyurethanes as disclosed by Haefele in U.S. Pat. No. 3,465,759; and paper as disclosed by Bonilla in U.S. Pat. No. 2,991,790.

The Bonilla patent discloses treatment of end wraps with chemical agents so that the waving solution is counteracted before reaching the hair ends. Treatment of end wraps with citric acid to counteract the waving solution and thereby protect hair ends is also known in the art.

There is, however, a continuing need to simplify the waving process. This object is achieved in the current invention by providing chemically modified end wraps.

SUMMARY OF THE INVENTION

The present invention provides an end wrap containing hair-waving chemicals. The end wrap is activated by contact with a solution. Optionally, the end wrap is dissolved or disintegrated by the solution. A kit for the end wraps and chemicals is included.

Also included in the invention is a method for waving hair. In this method, sections of hair are wrapped with end wraps containing hair-waving activating chemicals. The hair is waved by contacting the end wrapped hair with solution to activate the hair softening chemicals, then an oxidizing agent is added. The end wraps are dissolved or disintegrated by rinsing them out of the hair.

The waving system of the present invention eliminates separate mixing of aqueous chemical solutions, reduces spillage, dripping, overprocessing and other problems associated with conventional methods. Waving of hair is thus economically facilitated. This process is applicable for use with all hair types and variations, including dyed, damaged and thin hair.

DETAILED DESCRIPTION OF THE INVENTION

The invention is drawn to an end wrap for use in waving hair, a method of waving hair, and a kit to facilitate the method.

The end wrap consists of a water sensitive substrate with a hair softening chemical dispersed within or upon said substrate. Optionally, the end wrap also contains a means for activating the hair softening chemical. A method of producing the end wrap includes preparing a solution of a reducing agent and applying the reducing agent to the end wraps. Alternatively, the reducing agent may be microencapsulated and incorporated into the end wrap.

As used herein, "containing," "dispersed within or upon," or "dispersed therein or thereon" includes impregnating, immobilizing, coating, and dispersing chemicals in or on the substrate.

A method of producing the end wrap comprises preparing a solution of a polyvinylpyrrolidone resin, such as Gantrez ® (GAF), in anhydrous ethanol. Other water sensitive polymers such as homopolymers and copolymers of vinyl alcohol, vinylpyrrolidone, vinyl methylethers, acrylamides, acrylic acids, maleic anhydride, natural and modified natural polymers, cellulose ethers, alkoxylated celluloses, chitosan, chemically modified chitosans, starch ethers, hydroxyethyl ethers, gelatins, poly(vinyl alkyl ether) copolymers with maleic anhydride and the like may also be used.

Water solubility, water swellability, and water sensitivity can be adjusted by appropriate copolymer selection and by selecting appropriate amounts and types of chemical cross-linking. The above list of polymers may be used to immobilize hair treating chemicals and as binders for soluble end wraps.

A suitable amount of thioglycolic acid is dissolved into the alcohol solution of the resin. Typically, 5 to 40% by weight of acid is adequate, preferably 8 to 12%. The thioglycolic acid is a reducing agent for reducing keratin disulfide bonds and is preferably, but not necessarily, substantially anhydrous. Other hair softening chemicals also may be used, such as thiolactates, bisulfites, thio acid esters, and similar chemicals, as well as chemicals which react directly with the protein structure of hair to impart waves without requiring cysteine-cysteine breakage and reformation chemistry, such as reactive urethanes, epoxies and the like. Ammonia gas is introduced into the mixture to form, in situ, substantially anhydrous ammonium thioglycolate, either dissolved or as a colloidal dispersion. Alternatively, organoamines such as alkanolamines can be used in place of ammonia to form the corresponding amine compound in situ.

The ammonium thioglycolate resin solution is dispersed within or upon a substrate material, such as Dissolvo ® (CMS Gilbreth). Other substrates include superabsorbent fabric, a fabric in which Fibersorb ® SAF superabsorbent fiber (Arco Chemical Company, Newtown Square, Pa.) is coblended with one or more other fibers to produce non-wovens with a range of physical properties and degrees of superabsorbency; one example is 20% Fibersorb ®, 20% rayon, and 60% polyester. Films or foams of other hydrophilic polymers also may be used; examples are partially crosslinked hydroxypropyl cellulose, hydrophilic polyurethanes and similar substrates.

After drying to remove alcohol solvent and any residual moisture, the end wrap contains 1-10 mg/in$^2$, preferably 3-5 mg/in$^2$, of ammonium thioglycolate. When using thioglycolate derivatives of higher molecular weight, the corresponding amounts of chemicals are increased proportionally in order to release sufficient active agent for hair softening.

The end wrap may also be in the form of a multi-layered substrate in which conditioners, proteins, penetrants, surfactants, and the like are dispersed in separate layers. Activation of the chemicals is accomplished by means of specific activating solutions or via use of timed release compositions.

Hair treating chemicals that may be incorporated into the end wraps include conditioners such as lanolin, specifically PET-75 lanolin; Ceteareth-5; Choleth-24; and Oleth-20. Examples of proteins are hydrolyzed silk protein, hydrolyzed keratin, collagen quaternaries, and placental extracts; examples of penetrants are glycerine, propylene carbonate, urea, methylol urea; examples of surfactants are sodium cocoyl isothionate, betaine and glycinate amphoterics, fatty acid amine oxides, and sulfosuccinate.

The design of the end wrap involves several considerations. The polymer, such as polyvinylpyrrolidone resin, should be chemically inert to the thioglycolate or other hair softening chemical, should form a tack-free film that is sufficiently flexible to allow the finished end wrap to be wrapped with sections of hair on a rod without rupturing the resin layer, and the rate of solution of the activating agent in water should closely match the rate of swelling of the substrate, and should be complete as the substrate reaches the fully swollen state.

The soluble end wrap should swell to a sponge-like consistency when in contact with thoroughly wetted hair, but not completely dissolve. The end wrap should completely dissolve or disintegrate when subjected to a large excess of water or aqueous solutions of salts and/or surfactants that enhance wetting and penetration.

Thus, chemicals which are reactive with hair are dispersed in or on resinous or polymeric matrices that are controllably soluble in water. The examples use the monolithic approach, however, alternate immobilization techniques such as microencapsulation, microspheres, liposomes, absorptive solids, and the like may be employed with equal ease.

For example, thioglycolate encapsulated in a water-sensitive but alcohol insoluble wall material may be used as a dispersion in an alcohol resin solution to coat the soluble substrate. One skilled in the art of controlled release technology would be aware of other appropriate wall materials, carriers, and coatings. Similarly, thioglycolic acid may be immobilized in an alkali soluble resin, polyvinyl alkyl ether copolymers with maleic anhydride for example.

The invention also includes a method of waving hair using the end wraps of the invention. The hair waving process comprises the steps of wetting the hair and dividing the hair into a plurality of individual sections to be waved. An end wrap containing a hair softening chemical is applied to the ends of the hair of one section. The end wrapped hair is wound onto a substantially cylindrical rod and the rod is secured in place. End wraps are applied to each of the sections of hair to be waved and each section is wrapped and secured into place until all of the hair to be waved is end-wrapped, wound onto a rod, and secured. The wound, end-wrapped hair is thoroughly wetted with water or an aqueous surfactant solution, e.g. 0.1 to 10.0% ammonium carbonate/ethoxylated nonylphenol (Triton ® x-100, Rohm & Haas) to activate the hair softening chemical. Optionally, the activation step may be signalled by effervescence, resulting from reaction of citric acid and sodium bicarbonate contained separately in the release layer, to assist the hair care professional in determining if the reducing agent has been released. The substrate swells and releases the thioglycolate, which becomes very rapidly diluted by the water or surfactant solution. The swelling action tightens the wrapped sections of hair and accelerates the transfer of the hair softening chemicals to the hair to initiate the softening process.

On normal hair, the optimum wave generally forms in about 5-10 minutes. When the desired wave is achieved, the wound, end-wrapped hair is treated with an ionic, water soluble oxidizing agent or neutralizer such as a hydrogen peroxide/phosphonic acid mixture or a sodium bromate/sodium citrate mixture, which reforms substantially all the keratin disulfide bonds. The hair is rinsed after sufficient time has passed for the oxidizing agent to act and the rods are removed. The hair is loosened and rinsed again with water to remove the chemicals and swollen end wraps, eliminating the need to remove them manually.

Optionally, when the thioglycolic acid is immobilized in an alkali soluble resin such as a polyvinyl alkyl ether/maleic anhydride copolymer, the substrate may be wrapped on wet hair and the thioglycolate not activated until the full head of hair is wrapped. Once the full head of hair is wrapped, an alkaline solution of buffered ammonium carbonate is applied to dissolve the binder resin. Accordingly, because the binder resin is dissolved during the activation step, it is unnecessary to rinse the resin out of the hair after waving is complete. Thioglycolic acid is activated and reacts with the ammonium salt to form ammonium thioglycolate, thus providing the desired pH of 8-9 for optimum softening and waving of the hair. Excess ammonium carbonate decomposes with both $NH_3$ and $CO_2$ volatilizing and reducing the pH from 8-9 to about 5-6. This latter pH change allows the swollen hair to shrink and regain some of its body. The evolved $CO_2$ can supplement the effervescence from the citrate/bicarbonate mixture.

The following examples are provided for illustrative purposes only and are not to be interpreted so as to unnecessarily limit the invention to less than the full range of equivalents to which it is entitled.

EXAMPLE 1

An hydrophobic colloidal silica, Cab-o-sil PTG, (Cabot Corporation) was treated separately with Zotos, Helene Curtis and Russ Kalvin Part A (reducing) commercial permanent wave solutions (90% water/10% active ingredient). The silica gelled the Zotos, Helene Curtis and Russ Kalvin wave solutions to pastes at 7-10% by weight. The Zotos, Helene Curtis and Russ Kalvin-containing silica gels dissolved instantly in water.

EXAMPLE 2

An hydrophobic colloidal silica, Cab-o-sil PTG, was treated separately with Zotos, Helene Curtis and Russ Kalvin Part A (reducing) commercial permanent wave solutions (90% water/10% active ingredient). The silica gelled the Zotos, Helene Curtis and Russ Kalvin wave solutions to putty-like consistencies at 15-20% by weight. The Zotos, Helene Curtis and Russ Kalvin-containing silica gels dissolved instantly in water as in Example I.

EXAMPLE 3

An hydrophobic colloidal silica, TS-720, (Cabot Corporation) was treated separately with Zotos, Helene Curtis, and Russ Kalvin Part A (reducing) commercial permanent wave solutions (90% water/10% active ingredient). The TS-720 gelled the Zotos, Helene Curtis and Russ Kalvin wave solutions to pastes at 7-10% by weight. The Zotos, Helene Curtis and Russ Kalvin-containing silica gels required two minutes to dissolve in water.

EXAMPLE 4

An hydrophobic colloidal silica, TS-720, was treated separately with Zotos, Helene Curtis, and Russ Kalvin Part A (reducing) commercial permanent wave solutions (90% water/10% active ingredient). TS-720 gelled the Zotos, Helene Curtis and Russ Kalvin wave solutions to putty-like consistencies at 15-20% by weight. The Zotos, Helene Curtis and Russ Kalvin-containing silica gels required two minutes to dissolve in water.

EXAMPLE 5

The pastes of EXAMPLE 3 were applied to Dissolvo 2800 soluble papers and the treated papers applied to the ends of wet sectioned hair. Superior curl resulted from the Dissolvo wave-paste containing papers as compared to ungelled commercial permanent wave solution.

EXAMPLE 6

The putties of EXAMPLE 4 were applied to Dissolvo 2800 soluble papers, allowed to dry, and then immersed in water. Dissolution of the treated papers began in about 30 seconds and was complete in about 2 minutes.

EXAMPLE 7

Carbowax ® resins (Union Carbide) were also tested as slow release binders. A 50/50 by weight dry mixture of citric acid and sodium bicarbonate was dispersed in melts of Carbowaxes 20M, 750M, and 540M at levels of 0.5% and 1.5% by weight. Melt dispersions were coated/impregnated into end wraps such as Revlon's Realistic Styling End Wraps; Dissolvo 2800, and *Fibersorb* SAF fabric. The 20M systems showed extensive effervescence as evidenced by gas evolution from substrate surfaces when totally immersed in water. Both Dissolvo 2800 and SAF gradually expanded during effervescence. The conventional end wraps did not swell. Surface coating on each of the above Carbowax coated substrates with TS-720 silica gave additional delayed gas release. Gas release followed an S-shaped curve versus time of water immersion with 7-8 minutes as maximum release time.

ACS Reagent grade acetic acid (99.7%) was used to simulate thioglycolic acid. The acetic acid was dispersed at 0.1% and 0.2% by weight in molten (150° F.) Carbowax 20M. The Carbowax 20M containing acetic acid was coated/impregnated onto each of SAF and Dissolvo 2800 and over coated with plain molten 20M to seal the surface. Test strips were then immersed in 2% aqueous sodium bicarbonate solution and $CO_2$ evolution versus time was monitored as shown in Table I.

TABLE I

| | Immersion time (minutes @ RT) in Bicarbonate solution | | | |
|---|---|---|---|---|
| | Dissolvo 2800 | | SAF | |
| | 0.1% acid | 0.2% acid | 0.1% acid | 0.2% acid |
| GE onset | 1.5-2 | 1 | 1-1.5 | <1 |
| High rate GE | 2-4.5 | 1.5-3 | 2-4 | 1-3.5 |
| Slow rate GE | 4.5-7 | 3-3.5 | 4-7 | 3.5-4.5 |
| End GE | 7 | 4-5 | 7-8 | 5-6 |

GE = Gas Evolution

Other hair treating products may similarly be used in the method disclosed above. For example, tints, dyes, mousses and the like may also be applied to the hair by the method of the present invention.

Also included in the present invention is a kit to facilitate the method of waving hair. The kit includes a water-sensitive substrate having a hair softening chemical dispersed therein; an ionic, water soluble oxidizing agent for reforming substantially all the keratin disulfide bonds; and substantially cylindrical rods for winding end-wrapped hair sections thereabout.

While this invention has been disclosed with reference to a specific embodiment, it is apparent that other embodiments and equivalent variations of this invention may be devised by those skilled in the art without departing from the true spirit and scope of this invention. The appended claims are intended to be construed to include all such embodiments and equivalent variations.

What is claimed is:

1. An end wrap for use in waving hair comprising:
   a. a controllably water soluble substrate,
   b. a binder dispersed within said substrate, and
   c. an alkali-sensitive hair softening chemical dispersed within said binder,
   said end wrap adapted for use with wet hair.

2. An end wrap of claim 1 wherein said substrate is an alkali-soluble resin.

3. An end wrap of claim 1 wherein said hair softening chemical is a reducing agent for reducing keratin disulfide bonds.

4. An end wrap of claim 3 wherein said hair softening chemical is selected from the group consisting of thioglycolates, bisulfites, thiolactates, thioacid esters, epoxies, and urethanes.

5. An end wrap of claim 4 wherein said thioglycolates are selected from the group consisting of ammonium thioglycolate, sodium thioglycolate and glyceryl monothioglycolate.

6. An end wrap of claim 3 wherein said substrate is dissolvable.

7. An end wrap of claim 3 wherein said substrate swells and releases said hair softening chemical, such that the swelling of said substrate compresses and tightens the wound hair and distributes said hair softening chemical thus imparting wave to said hair.

8. An end wrap of claim 3 wherein said substrate comprises a plurality of layers, said hair softening chemical dispersed on one layer and other hair treating products dispersed on other layers.

9. An end wrap of claim 8 wherein said other hair treating products are selected from the group consisting of conditioners, proteins, penetrants, neutralizers, dyes, tints, mousses, and surfactants.

10. An end wrap of claim 8 wherein said other hair treating products are selected from the group consisting of lanolin, Ceteareth-5, Choleth-24 and Oleth-20.

11. An end wrap of claim 8 further including a means for activating said hair softening chemical.

12. An end wrap of claim 11 wherein the release of said means for activating the hair softening chemical and the release of said other hair treating products from the substrate are separately initiated.

13. An end wrap of claim 11 wherein said means for activating said other hair softening chemical and said other hair treating products are timed release compositions.

14. An end wrap for use in waving hair comprising:
a. a controllably water soluble paper substrate,
b. a binder dispersed within said substrate, and
c. an alkali-sensitive hair softening chemical dispersed within said binder,
said end wrap adapted for use with wet hair.

15. An end wrap of claim 14 wherein said hair softening chemical is ammonium thioclycolate.

16. An end wrap for use in waving hair comprising:
a. a polymeric hydrophilic controllably water soluble substrate, and
b. a binder dispersed within said substrate, and
c. an alkali-sensitive hair softening chemical dispersed within said binder,
said end wrap adapted for use with wet hair.

17. An end wrap of claim 16 wherein said polymeric hydrophilic controllably water soluble substrate is a water-sensitive polyvinylpyrrolidone substrate.

18. An end wrap of claim 16 wherein said hair softening chemical is ammonium thioglycolate.

19. A kit for cold waving hair comprising:

a. a controllably water soluble substrate, a binder dispersed within said substrate, and an alkali-sensitive hair softening chemical dispersed within said binder, which is a reducing agent for substantially reducing keratin disulfide bonds,
b. an ionic, water soluble oxidizing agent for reforming substantially all the keratin disulfide bonds, and
c. substantially cylindrical rods for wrapping hair thereabout,
said end wrap adapted for use with wet hair.

20. A method of cold waving hair comprising:
a. wetting hair;
b. dividing the hair into a plurality of individual hair sections to be waved;
c. applying an end wrap having an anhydrous hair softening chemical dispersed therein, which is a reducing agent for reducing keratin disulfide bonds, to the ends of one section of hair;
d. winding the end-wrapped hair of step c. onto a substantially cylindrical rod and securing said rod into place;
e. repeating steps b. and c. until all of the hair sections are end-wrapped and wound;
f. thoroughly wetting the wound hair with water to activate the reduction of keratin disulfide bonds;
g. waiting for a time sufficient to effect the desired reduction;
h. treating the wound hair with an oxidizing agent;
i. rinsing the wound hair after sufficient time has passed for the oxidizing agent to act;
j. removing said cylindrical rods and loosening the wound hair; and
k. rinsing the hair with water to remove chemicals and end wraps.

21. A method of cold waving hair according to claim 20 wherein said activation of the reduction of keratin disulfide bonds is signalled by effervescence.

22. An end wrap for use in waving hair comprising:
a. a controllably water soluble substrate,
b. a binder dispersed within said substrate, and
c. an alkali-sensitive hair softening chemical dispersed within said binder wherein said hair softening chemical is anhydrous,
said end wrap adapted for use with wet hair.

23. An end wrap for use in waving hair comprising:
a. a controllably water soluble substrate,
b. a binder dispersed within said substrate, and
c. an alkali-sensitive hair softening chemical dispersed within said binder wherein said hair softening chemical is microencapsulated,
said end wrap adapted for use with wet hair.

* * * * *